(12) United States Patent
Bastide et al.

(10) Patent No.: US 12,080,396 B2
(45) Date of Patent: Sep. 3, 2024

(54) RISK BASED PRESENTATION OF HEALTHCARE PROTOCOLS

(71) Applicant: International Business Machines Corporation, Armonk, NY (US)

(72) Inventors: Paul R. Bastide, Ashland, MA (US); Matthew E. Broomhall, Goffstown, NH (US); Robert E. Loredo, North Miami Beach, FL (US)

(73) Assignee: International Business Machines Corporation, Armonk, NY (US)

( * ) Notice: Subject to any disclaimer, the term of this patent is extended or adjusted under 35 U.S.C. 154(b) by 297 days.

(21) Appl. No.: 16/872,933

(22) Filed: May 12, 2020

(65) Prior Publication Data
US 2021/0358584 A1 Nov. 18, 2021

(51) Int. Cl.
| | |
|---|---|
| *G16H 70/20* | (2018.01) |
| *G06F 16/9538* | (2019.01) |
| *G06F 40/106* | (2020.01) |
| *G06F 40/295* | (2020.01) |
| *G16H 15/00* | (2018.01) |
| *G16H 50/30* | (2018.01) |
| *G16H 50/70* | (2018.01) |

(52) U.S. Cl.
CPC ......... *G16H 15/00* (2018.01); *G06F 16/9538* (2019.01); *G06F 40/106* (2020.01); *G06F 40/295* (2020.01); *G16H 50/30* (2018.01); *G16H 50/70* (2018.01); *G16H 70/20* (2018.01)

(58) Field of Classification Search
CPC ........ G16H 15/00; G16H 50/30; G16H 70/20; G16H 50/70; G06F 40/295; G06F 40/106; G06F 16/9538
See application file for complete search history.

(56) References Cited

U.S. PATENT DOCUMENTS

| | | | |
|---|---|---|---|
| 2012/0154582 A1* | 6/2012 | Johnson | G16H 40/20 340/521 |
| 2012/0284631 A1* | 11/2012 | Lancioni | G06F 8/38 715/744 |

(Continued)

FOREIGN PATENT DOCUMENTS

WO 2015023674 A1 2/2015

*Primary Examiner* — Chad A Newton
(74) *Attorney, Agent, or Firm* — Edell, Shapiro & Finnan, LLC (57) ABSTRACT

A system and method of visually displaying healthcare protocols to a user receives from the user, via an electronic communications network, search term(s) associated with a health-related condition. A corpus of document(s) stored in an electronic format is identified with a computer and, based on the search term(s), at least one of the document(s) is analyzed with the computer for a treatment protocol associated with the health-related condition. First content for presentation to the user is determined with the computer, the first content including at least a portion of the treatment protocol associated with the health-related condition. A risk value indicative of risk(s) associated with the first content is determined. In response to a determination that the risk value exceeds the risk threshold, second content for presentation is determined by reformatting the first content. A message is sent causing the second content to be visually displayed to the user.

18 Claims, 6 Drawing Sheets

(56) References Cited

U.S. PATENT DOCUMENTS

| | | | |
|---|---|---|---|
| 2013/0218600 A1* | 8/2013 | Lynn | G16H 50/70 |
| | | | 705/3 |
| 2014/0350351 A1* | 11/2014 | Halperin | A61B 5/6892 |
| | | | 600/300 |
| 2015/0095044 A1 | 4/2015 | Hartman et al. | |
| 2016/0239611 A1 | 8/2016 | Heldt et al. | |
| 2016/0378952 A9* | 12/2016 | Lynn | G16H 50/70 |
| | | | 705/3 |
| 2017/0140109 A1 | 5/2017 | Kheifetz et al. | |
| 2017/0278209 A1* | 9/2017 | Olsen | G16H 10/60 |
| 2017/0286622 A1* | 10/2017 | Cox | G16Z 99/00 |
| 2018/0046764 A1* | 2/2018 | Katwala | G16H 15/00 |
| 2018/0247023 A1* | 8/2018 | Divine | G16H 20/40 |

* cited by examiner

RISK BASED PRESENTATION OF HEALTHCARE PROTOCOLS

BACKGROUND

1. Technical Field

Present invention embodiments relate to computer systems and methods for presenting healthcare protocols to a user, and more specifically, to computer systems and methods for risk-based presentation of healthcare protocols to a user.

2. Discussion of the Related Art

Documents including information related to healthcare are readily available via mobile and web applications and websites to a variety of consumers of those documents, including lay persons and those with more experience and/or education. The reach of these documents is extended through applications such as search engines and indices. Users of these applications may search for a potential treatment or protocol concerning a health-related condition. The users may be presented with snippets or summaries of documents found from the search. However, these snippets or summaries are generated irrespective of the risk associated with misunderstanding or incorrectly following some or all of the treatment or protocol. That is, risk levels associated with user miscomprehension of the snippets or summaries are not considered in the determination of what information is included in the snippers or summaries. Thus, there remains a need to enhance presentation of treatment protocols while minimizing risk.

SUMMARY

According to one embodiment of the present invention, a method of visually displaying healthcare protocols to a user is provided. The method comprises receiving from the user, via an electronic communications network, one or more search terms associated with a health-related condition. A corpus of one or more documents stored in an electronic format is identified with a computer and based at least on the one or more search terms. At least one document of the corpus is analyzed with the computer for a treatment protocol associated with the health-related condition. First content for presentation to the user is determined with the computer, the first content comprising at least a portion of the treatment protocol associated with the health-related condition. A risk value indicative of one or more risks associated with the first content for presentation is determined with the computer. A determination is made, with the computer, whether the risk value exceeds a risk threshold. In response to determining, with the computer, the risk value exceeds the risk threshold, second content for presentation is determined, with the computer, by reformatting the first content for presentation. A message is sent, via the electronic communications network, causing the second content to be visually displayed to the user. Embodiments of the present invention further include a system and computer program product for visually displaying healthcare protocols to a user.

BRIEF DESCRIPTION OF THE DRAWINGS

Generally, like reference numerals in the various figures are utilized to designate like components.

DETAILED DESCRIPTION

Present invention embodiments analyze documents for treatment protocols associated with health-related conditions and reformat content for presentation based on risks associated with presentation of some or all of the treatment protocol to a user. For example, a corpus of one or more documents stored in an electronic format may be determined to be associated with a health-related condition treatment protocol, a risk of displaying the treatment protocol or a subset of the treatment protocol may be calculated based on an analysis of the content of the document and a portion of the protocol corresponding to the search, and a determination may be made whether to reformat presentation of the search result corresponding to the document based on the risk analysis.

Present invention embodiments may limit miscomprehension associated with presentation of a treatment protocol associated with a health-related condition to a user.

Present invention embodiments may analyze a treatment protocol associated with a health-related condition to determine one or more risks associated with presenting content including some or all of the treatment protocol to a user, and may modify the content, based on the one or more determined risks, to include information that reduces potential miscomprehension associated with presentation of the treatment protocol.

Present invention embodiments may determine a risk of presenting to a user a portion of a treatment protocol dependent on another portion of the treatment protocol and corresponding to search terms or other input from a user, and may reformat presentation of the portion of the treatment protocol in such a way as to reduce the determined risk.

Present invention embodiments provide improvements in document search technology and search result user interfaces. Present invention embodiments may enhance generation and/or presentation of a document summary, snippet, or preview generated for a search.

Figure 1:
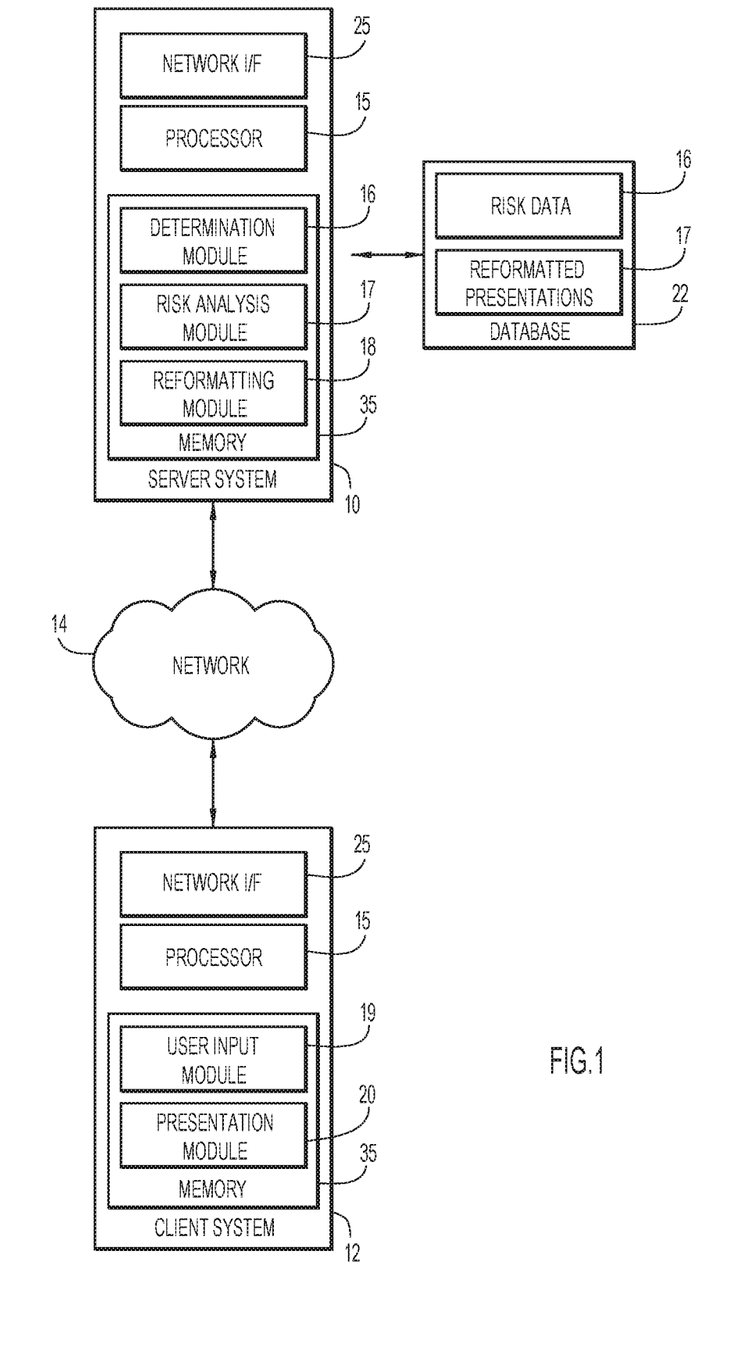
FIG. 1 is a diagrammatic illustration of an example computing environment implementing an embodiment of the present invention.

An example environment for use with present invention embodiments is illustrated in FIG. 1. Specifically, the environment includes one or more server systems 10, and one or more client or end-user systems 12. Server systems 10 and client systems 12 may be remote from each other and communicate over a network 14. The network may be implemented by any number of any suitable communications media (e.g., wide area network (WAN), local area network (LAN), Internet, Intranet, etc.). Alternatively, server systems 10 and client systems 12 may be local to each other, and communicate via any appropriate local communication medium (e.g., local area network (LAN), hardwire, wireless link, Intranet, etc.).

Client systems 12 may enable users, via user input module 19 and/or presentation module 20, to enter a set of one or more search terms, view and/or select results of the search, and/or view and/or select one or more documents (e.g., documents for analysis to identify a treatment protocol associated with a health-related condition, documents for analysis to determine risks associated with the treatment protocol, etc.). The client systems 12 may present a user interface, such as a graphical user interface (GUI) or other interface (e.g., command line prompts, audio prompts, etc.) to solicit information from users pertaining to the health conditions and documents, and may provide information including analysis results and information associated with results (e.g., search results, document data, document content, etc.). Client systems 12 may include various types of user input devices, such as a mouse, a keyboard, a touch pad, a microphone, etc., to accept input from users. The set of search terms may be provided to server systems 10 to determine documents pertaining to the search terms, analyze documents pertaining to the search results, and/or to perform a risk analysis pertaining to presentation of some or all of a treatment protocol in the documents. Server systems 10 may re-format search results based on such a risk analysis and send messages to client systems 12 causing the risk-based re-formatted search results to be presented to the user (e.g., visually and/or audibly).

A database system 22 may store various information for the analysis (e.g., risk information, document information, reformatting information, a labeled dictionary, reformatted presentations). The database system may be implemented by any conventional or other database or storage unit, may be local to or remote from server systems 10 and client systems 12, and may communicate via any appropriate communication medium (e.g., local area network (LAN), wide area network (WAN), Internet, hardwire, wireless link, Intranet, etc.).

Figure 6:
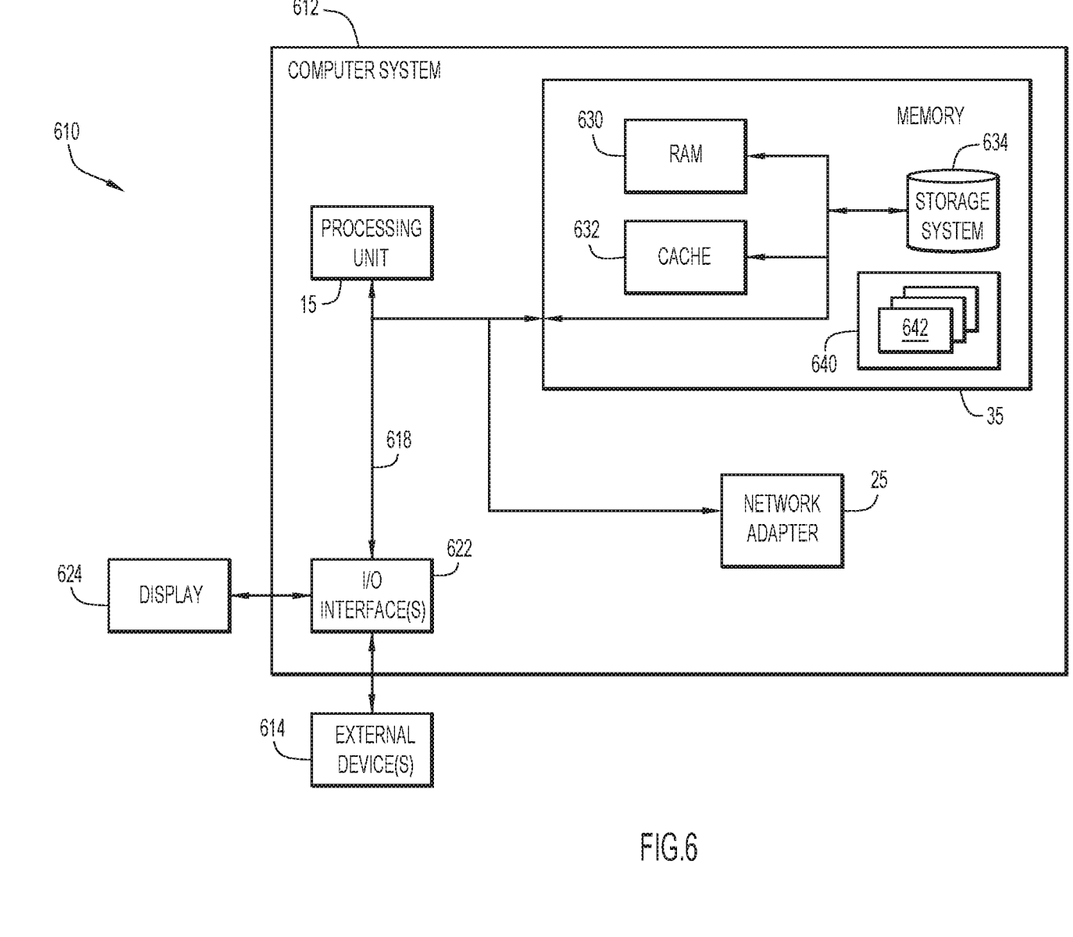
FIG. 6 is a block diagram of an example computing device according to an embodiment of the present invention.

Server systems 10 and client systems 12 may be implemented by any conventional or other computer system or device preferably equipped with a display or monitor, a base (e.g., including at least one hardware processor 15 (e.g., microprocessor, controller, central processing unit (CPU), etc.), one or more memories 35 and/or internal or external network interfaces or communications devices 25 (e.g., modem, network cards, etc.)), optional input devices (e.g., a keyboard, mouse or other input device), and any commercially available and custom software (e.g., server/communications software, module, browser/interface software, etc.). An example computing device according to an embodiment of the present invention is shown in FIG. 6 and described in greater detail below.

Alternatively, one or more client systems 12 may analyze documents to determine risk pertaining to presentation of at least part of treatment protocols of the documents and reformatting presentation of search results (e.g., when risk is determined to be an unacceptable level) when operating as a stand-alone unit. In a stand-alone mode of operation, the client system stores or has access to the data (e.g., corpus of one or more documents, risk information), and includes modules to determine a treatment protocol, determine risk associated with presenting the treatment protocol, and reformat presentation of the treatment protocol if the determined risk is unacceptable. The user interface may solicit information from a corresponding user pertaining to the desired documents and analysis, and may provide reports including analysis results.

In an example embodiment, one or more server systems 10 may include a treatment protocol determination module 16 for receiving from a user one or more search terms associated with a health-related condition, identifying a corpus of one or more documents stored in an electronic format based at least on the one or more search terms, analyzing a document of the corpus for a treatment protocol associated with the health-related condition, and determining content including at least a portion of the treatment protocol for presentation to the user. Example embodiments may provide access to the treatment protocol determination module 16 locally and/or remotely, e.g., via a web browser, client application, or other user interface.

The treatment protocol determination module 16 analyzes one or more documents to determine if any treatment protocols are in the one or more documents. The treatment protocol determination module 16 may analyze a document for information indicative of a treatment protocol based on information from one or more sources, which may be considered independently or in some combination. For example, the treatment protocol determination module 16 may analyze a document for information indicative of a treatment protocol associated with a health-related condition based on one or more search terms or other input from a user, content of the document, document formatting information of the document, metadata of the document, and/or any other suitable information.

The treatment protocol determination module 16 determination that the document includes a treatment protocol may include extracting the treatment protocol from the document. The treatment protocol determination module 16 may use natural language processing to extract the treatment protocol from the document. For example, to extract a treatment protocol from a document, the natural language processing may utilize one or more of the following: formatted headings; numbered formatting; numbered hierarchies; bulleted lists; protocol formatted elements (e.g., prescriptive block and/or special format); specific action elements and/or declarative statements (e.g., rest the knee, ice the knee); prefixed statements indicative of a prescribed action; tagged action elements using resource description framework (RDF) and/or semantic tags; and any other information that may be indicative of the document including a treatment protocol. Contextual information related to the protocol may be extracted and analyzed using natural language processing by identifying intents and/or entities. For example, intents, such as actions to be performed by a user or patient (e.g., "take after dinner," "take only as needed," etc.) may be identified, and entities performing the action (e.g., user, patient, doctor, nurse, etc.), entities used in performing an action (e.g., medicated gel, dressing, etc.), and entities on which an action is performed (e.g., an affected area, an injured body part, etc.) may be identified. As another example, in the statement "change dressing after each application of medicated gel," the dressing and the gel (or medicated gel) may be identified as entities and the action may be determined to be the changing of the dressing along with applying the gel to the affected area.

The treatment protocol determination module 16 may analyze the document to identify each step of a plurality of steps of a treatment protocol. For one or more steps of a plurality of steps of the treatment protocol, the module 16 may analyze a step to determine a dependency of the step to one or more other steps of the treatment protocol. For example, the module 16 may determine that the fourth step of a protocol including four steps is dependent on the three preceding steps, or in other words, the fourth step is dependent upon the first, second, and third steps. Dependency of a step may be used in determining risk, as described in more detail below.

The treatment protocol determination module 16 may communicate with, or be integrated with, a search engine and/or an intelligent virtual assistant. For example, treatment protocol determination module 16 may include a search engine, and one or more predefined and/or dynamically created search queries may be executable by the search engine to obtain information for analysis by the determination module 16 and/or other modules. For example, as part of a search engine's extraction routine, natural language processing (e.g., using open XML format, PDF processing utilities, etc.) may be used to extract document elements such as names to identify treatment protocols, determine formatting in the document, and other information. The search engine in communication with, or integrated with, the treatment protocol determination module 16 may be configured to normally return search results in the form of snippets or summaries (e.g., a predetermined number of words or lines of text), by default.

Server systems 10 may also include a risk analysis module 17 for analyzing information that may be relevant to determining a risk associated with content for presentation. The risk analysis module 17 may analyze information obtained from one or more sources (e.g., from treatment protocol determination module 16, database 22, one or more applications running user's devices, etc.). Information that may be relevant to determining a risk may include content, content segments, snippets or summaries, risk analysis factors (e.g., weighting information, aggregation information, etc.), risk threshold values, and any other suitable information.

The risk analysis module 17 determines one or more risks of presenting a protocol (or a subset of a protocol) identified by the determination module 16. For example, the risk analysis module 17 may calculate, in the context of the protocol, risk of presenting an identified step of a protocol (e.g., identified by the determination module 16) to a user (e.g., without steps from which the identified step depends). The risk analysis module 17 may calculate risk of presenting a protocol or a subset of the protocol from one or more risk values according to several factors, which may be considered independently or in some combination. When considered as a combination, the factors may be weighted in some manner in order to increase the influence that some factors have over other factors when combined.

One such factor is a risk value associated with search terms and words, phrases, and/or actions corresponding to the protocol. The risk analysis module 17 may calculate the risk based at least in part on the risk levels associated with words, phrases, and/or actions of the protocol provided to the risk analysis module by the determination module 16. For example, the risk analysis module 17 may receive, from the determination module 16, natural language processing information for the protocol including words, phrases, and/or actions of the protocol stemmed by the determination module 16 and an indication of their corresponding steps. For example, risk may be determined based on risk levels associated with (e.g., mapped or assigned to) categories of activities (e.g., health conditions, exercise routines, etc.), medical language, associated actions (e.g., cut, sterilize, wrap, etc.), associated actors (e.g., doctor, nurse, internist, patient, user, physician's assistant, etc.), risk warnings (e.g., may cause harm, medical professional required, etc.), and/or references to specific people with skills, a number of occurrences of words and/or phrases, in a document. The risk analysis module 17 may compare the protocol or a subset of the protocol to a labeled risk dictionary to determine risk values, which may be aggregated together to determine a risk of presenting the protocol or a subset of the protocol. For example, the risk analysis module may receive or obtain risk values from a labeled risk dictionary that includes a database of various words, labels and/or phrases and associated risk values. As another example, a step in a protocol may be assigned a higher risk level if the step includes the word "doctor" performing an action, whereas a step in a protocol may be assigned a lower risk level if the step includes the word "user" performing an action. As yet another example, occurrence of doctor may increase a risk by +1, occurrence of patient may not increase or decrease risk (e.g., +0), and occurrence of scalpel may increase risk by +1000. An aggregate risk based on specific words and actions towards particular person or by a particular person may be calculated. A step in a protocol that includes cutting open a bag may be assigned a lower risk than a step including cutting open a person/patient. In an embodiment, the associating of actions such as cutting with objects such as a bag or person/patient are performed by the determination module 16, e.g., using natural language processing techniques such as named entity recognition (NER), parts of speech (POS) tagging, shallow parsing (or chunking), text summarization, and/or topic modeling.

Another factor is a dependency of a to-be-presented portion of the protocol on other portions of the protocol. For example, a step may be determined to be dependent on some or all steps of protocol, and a risk level may be determined for presenting the dependent step based on the determined dependency. For example, a dependency of a step that matches a search may be determined based on the steps that precede and follow the matching step. Some example techniques for determining dependency are described in more detail below in connection with FIG. 5.

Yet another factor is whether the protocol includes an adverse event. Terms in the protocol may be used to determine whether the protocol includes an adverse event, as defined in an adverse event database. For example, natural language text describing adverse events may be used in a comparison to terms in the protocol to identify matches or similarities to determine that the protocol mentions the possibility of an adverse event.

Prior search queries, search results, and reformatted presentations resulting therefrom may be stored (e.g., in the database 22 and/or memory 35). When a search query is received, a check for whether the reformatting has already been done based on the same or similar search may be conducted. If the same or similar search has been conducted, the same or similar search results were obtained, and reformatting has been done before, the risk analysis may be skipped and the reformatted content may be presented directly to the user.

Optional steps may be determined and excluded from the risk calculation. If presented to the user, these steps may be labeled as optional.

Server systems 10 may also include a reformatting module 18 for reformatting content for presentation to a user based on the indication of risk. Reformatting content for presentation based on the indication of risk may include adding information to the content to reduce possible user miscomprehension of the content, adding visual elements to the content to highlight risky portions of the content, adding a waiver for the user to provide an acknowledgment of associated risks, disallowing presentation of risky content, disallowing presentation of a portion of the treatment protocol in a summary or snippet form, presenting proceeding steps only after presenting preceding steps, forcing the user to open a document in full before presenting content of the document, or any other suitable addition, removal, or modification of information that enhances user comprehension risk of a treatment protocol. For example, the reformatting module 18 may receive from the risk analysis module 17 an indication that a risk value indicative of one or more risks associated with first content for presentation exceeds a risk threshold, and based on the indication, the reformatting module 18 may determine second content for presentation by reformatting the first content for presentation.

The reformatting module 18 reformats presentation of a default presentation format of the search engine (e.g., a snippet or summary typically returned as part of search results) for a document based on the determination of risk. For example, if there is an unacceptable level of risk determined with respect to presentation of the protocol in the default presentation format without reformatting, the reformatting module 18 may reformat presentation of the protocol in such a way that reduces the risk. In other words, the default presentation format for a document returned from a search may be too risky to present to a user without reformatting, and the reformatting module 18 may reformat the default presentation format so that the risk to the user is reduced. For example, the reformatting module 18 may include for presentation with the protocol a waiver and/or a warning. The warning may be a warning that includes text and/or symbol(s). The waiver and/or the warning may be based on the severity of risk, the protocol, etc. For example, it may be determined that presentation of a portion of the protocol corresponds to an unacceptable level of risk, but presentation of the entire protocol is less risky and corresponds to an acceptable level of risk. The reformatting module 18 may reformat presentation of the protocol to include the entire protocol. The reformatting module 18 may reformat content at least in part by modifying a markup language (e.g., hypertext markup language (HTML)) of a preview presentation of the treatment protocol.

Module 16 may include one or more modules or units to perform the various functions of present invention embodiments described below. The various modules (e.g., 16, 17, 18, 19, and 20) may be implemented by any combination of any quantity of software and/or hardware modules or units, and may reside within memory 35 of the server and/or client systems for execution by processor 15.

Modules 16, 17, 18, 19, and 20 may be combined into a single module. Alternatively, modules 16, 17, 18, 19, and 20 may be separate as shown, and it will be appreciated that one or more of the modules may each include one or more modules or units to perform the various functions of present invention embodiments described below. It will also be appreciated that present invention embodiments may be embedded into and/or couple with server systems 10.

Figure 2:
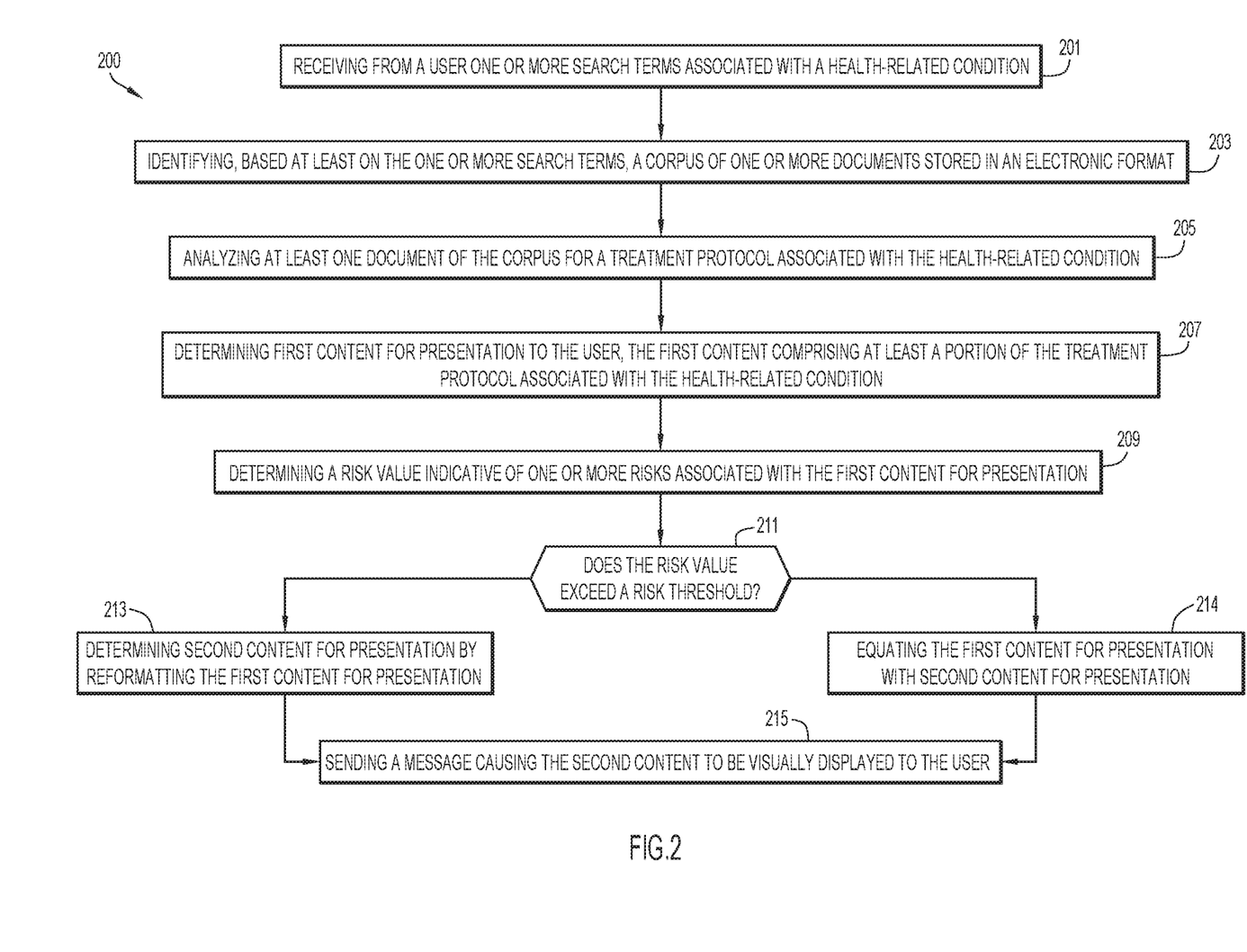
FIG. 2 is a procedural flowchart illustrating a manner of risk-based presentation of health care protocols according to an embodiment of the present invention.

FIG. 2 is a procedural flowchart illustrating a manner of risk-based presentation of healthcare protocols according to an embodiment of the present invention. Initially, one or more search terms associated with a health-related condition is received from a user at 201 (e.g., via determination module 16 and at least one server system 10). For example, server system 10 may be configured to receive one or more search terms associated with a health-related condition from user input module 19 on a client system 14 when client system 14 submits a search query.

In step 203, a corpus of one or more documents stored in an electronic format is identified based at least on the one or more search terms (e.g., via determination module 16 and at least one server system 10). In an example embodiment, a determination module 16 uses the one or more search terms to identify one or more documents stored in an electronic format that are related to the one or more search terms.

At 205, at least one document of the corpus is analyzed for a treatment protocol associated with the health-related condition. In an example embodiment, at least one document of the corpus is analyzed for a treatment protocol associated with a health-related condition by extracting the treatment protocol from the document based on at least one of a document heading, a numbered formatting, a numbered hierarchy, a bulleted list, an action element, or a declarative statement. In an example embodiment, at least one document of the corpus is analyzed for a treatment protocol associated with the health-related condition by segmenting the treatment protocol into a plurality of segments. Content for presentation may be reformatted by augmenting the segments with visual elements to visually indicate one or more risks associated with the segments.

In step 207, first content including at least a portion of the treatment protocol associated with the health-related condition is determined for presentation to the user. In an example embodiment, the first content for presentation corresponds to a subset of a plurality of steps of a treatment protocol. For example, the first content for presentation may be a snippet or summary of a document returned from a search for the health-related condition, and the snippet or summary may include at least a portion of the treatment protocol associated with the health-related condition. The first content for presentation may be determined by identifying a predetermined number of words or lines of text of the document based on the one or more search terms. For example, the first content for presentation may be determined by identifying a predetermined number of words or lines of text of the document that match the one or more search terms (e.g., according to a keyword search techniques). The first content may be determined to include at least a portion of the treatment protocol by analyzing the first content, for example, for: terminology or abbreviations related to medical treatments and/or conditions (e.g., "qd" meaning once a day, "b.i.d." meaning two times a day, etc.); medical code sets (e.g., the International Classification of Diseases (ICD), snomed clinical terms (snomed CT), etc.); pharmaceutical terminology or abbreviations; references to outlines, dependent steps, and/or temporal language (e.g., follow step 1); human anatomy; key words (e.g., directions, treatment, regime, protocol, etc.); previously labeled content (e.g., content that has previously been determined to be part of a protocol); and/or any other information that may be helpful in determining the first content includes at least a portion of the treatment protocol.

In step 209, a risk value indicative of one or more risks associated with the first content for presentation is determined. In an example embodiment, a risk value indicative of one or more risks associated with the first content for presentation is determined at least in part by identifying in the document a set of one or more terms for risk analysis, and comparing the set of one or more terms for risk analysis with a plurality of terms of a risk database. For example, the set of one or more terms for risk analysis may include words, phrases, actions, and/or other information of the first content identified from natural language processing. The set of one or more terms for risk analysis may be compared against the risk database to identify matches, and risk values of the matches (e.g., assigned or mapped to the matched terms) may be used to determine a risk value indicative of risk(s) associated with the first content. For example, one or more of the risk values may be selected to be used, individually or in combination (e.g., aggregated, weighted, etc.), to determine the risk value indicative of risk(s) associated with the first content.

The risk value indicative of risk(s) associated with the first content may be determined based at least in part on a dependency of the first content on other portions of the treatment protocol. The first content may be dependent on one or more steps or sub-steps of the treatment protocol or other portions of the document based on an order of treatment protocol. For example, the first content may be a step of a protocol with multiple steps, and it may be determined that the first content is dependent on step(s) or sub-step(s) of the treatment protocol that precede the first content, portion(s) of the document or another document referenced in the first content, and/or step(s) or sub-step(s) of the treatment protocol that are subsequent to the first content. For example, a dependency of the first content to other portions of the treatment protocol may be determined, and the determined dependency may affect the risk value indicative of risk(s) associated with the first content. For example, a risk value for first content that corresponds to a step of the protocol that is dependent upon one or more steps of the protocol may be higher than a risk value for first content that corresponds to a step of the protocol that is not dependent upon another step of the protocol, assuming all other factors are the same. The number of other steps that a step is dependent upon may affect the risk value. For example, risk for a step that is dependent on a preceding step that has risk may be dependent upon a distance or depth of the step from the preceding step. In other words, the number of steps in between the step and the preceding step may affect the risk of the step (e.g., a larger number of steps in between the step and the preceding step may indicate higher risk than a smaller number of steps in between the step and the preceding step). As an example, a risk value for the first content that corresponds to a step of the protocol may be determined to be dependent upon a step that is subsequent to the step. For example, if the first content corresponds to a step of "opening a wound" and a subsequent step corresponds to "closing the wound," then it may be determined that the step has a dependency on the subsequent step based on the reference to, involvement of, the same wound.

The risk value indicative of risk(s) associated with the first content may be calculated based on a number of missed steps (e.g., a number of steps that are missing from the first content in relation to the total number of steps of the protocol), an importance of step(s) (e.g., a severity of a step independent of another step), a compression of total details (e.g., a percentage of the protocol included in the first content), and a span of the steps (e.g., a number of steps that span a page).

The risk value indicative of risk(s) associated with the first content may be determined based at least in part on a category of the treatment protocol. For example, the treatment protocol of which the first content is a part may affect the risk value indicative of the risk(s) associated with the first content. For example, a treatment protocol in a category of invasive surgery may be attributed a higher risk than a treatment protocol in a category of minor cuts.

In step 211, a determination is made whether the risk value exceeds a risk threshold. For example, the determination may be made by comparing the risk value to the risk threshold. The risk threshold may be the same for all risk determinations, or the risk threshold may be set based on predetermined or dynamically determined associations of risk.

In steps 213 and 214, in response to a determination whether or not the risk value exceeds the risk threshold, second content for presentation is determined. In an example embodiment, the second content is the first content (i.e., the system determines that no re-formatting is necessary—e.g., because the risk value associated with presenting the first content does not exceed the risk threshold). In an example embodiment, the second content is different than the first content (i.e., the system determines that re-formatting is necessary—e.g., because the risk value associated with presenting the first content exceeds the risk threshold). In an example embodiment, determining the second content for presentation by reformatting the first content for presentation includes adding a risk warning and/or a waiver to the first content. For example, the waiver may be a consent form that allows the user to acknowledge that a partial summary of the protocol or less than the full protocol is going to be presented. In an example embodiment, the first content for presentation corresponds to a subset of a plurality of steps of the treatment protocol, and the second content for presentation includes at least one step of the plurality of steps of the treatment protocol that is not part of the subset. Determining which step(s) of the treatment protocol that is not part of the subset to include in the second content may be based on the effect on risk by including (e.g., whether including a step(s) that is not part of the subset would cause the risk to fall below the risk threshold) and/or a desired appearance of the presentation (e.g., whether including a step(s) that is not part of the subset would cause the presented content to span multiple pages, take up more than a desired amount of a display, etc.) For example, multiple steps that are not part of the subset may be included in the second content if adding a single step that is not part of the subset would not cause the risk to fall below the risk threshold.

In an example embodiment, determining the second content for presentation by reformatting the first content for presentation includes determining the least amount of information from the treatment protocol to add to the first content to cause the risk value of presenting the first content and the added information to be below the risk threshold, and adding the information to the first content. In other words, the first content may be reformatted, for example, to include the minimal amount of information that allows for an acceptable risk level.

Analyzing at least one document of the corpus for a treatment protocol associated with a health-related condition includes determining a dependency of the subset of the at least one step that is not part of the subset and determining a risk value indicative of one or more risks associated with the first content for presentation is based on the dependency of the subset to the at least one step that is not part of the subset.

In an example embodiment, determining second content for presentation by reformatting the first content for presentation comprises modifying a markup language of a preview presentation of the treatment protocol to disallow presentation of the first content in the preview presentation.

In step 215, a message causing the second content to be visually displayed to the user is sent. The message may include the second content or an indication of where the second content may be retrieved. For example, the message may include a webpage component file (e.g., HTML file, cascade style sheet file, JavaScript file, etc.) and may be sent to a web browser on a client device or system (e.g., client system 12). In an example embodiment, the second content may include audio or audio may be included in addition to the second content, and the audio may be caused to be presented audibly to the user.

Figure 3:
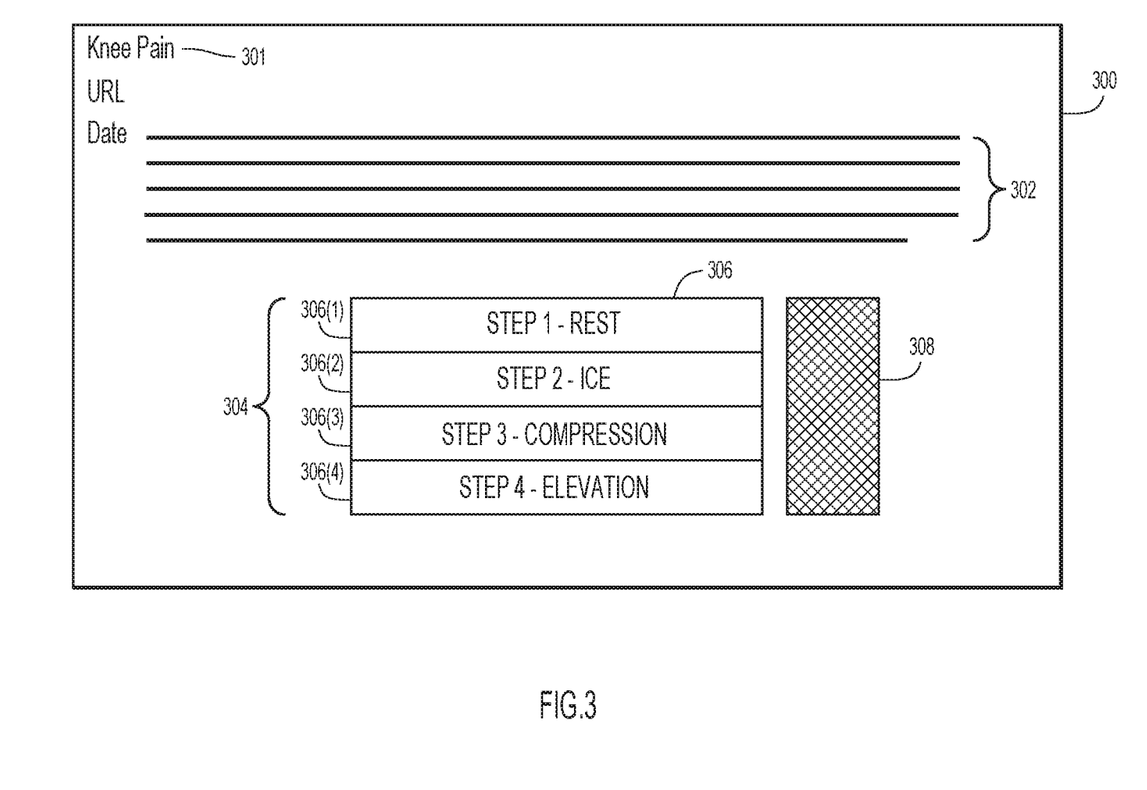
FIG. 3 is an example view of search results including a document that includes a treatment protocol associated with a health-related condition according to an embodiment of the present invention.
Figure 4:
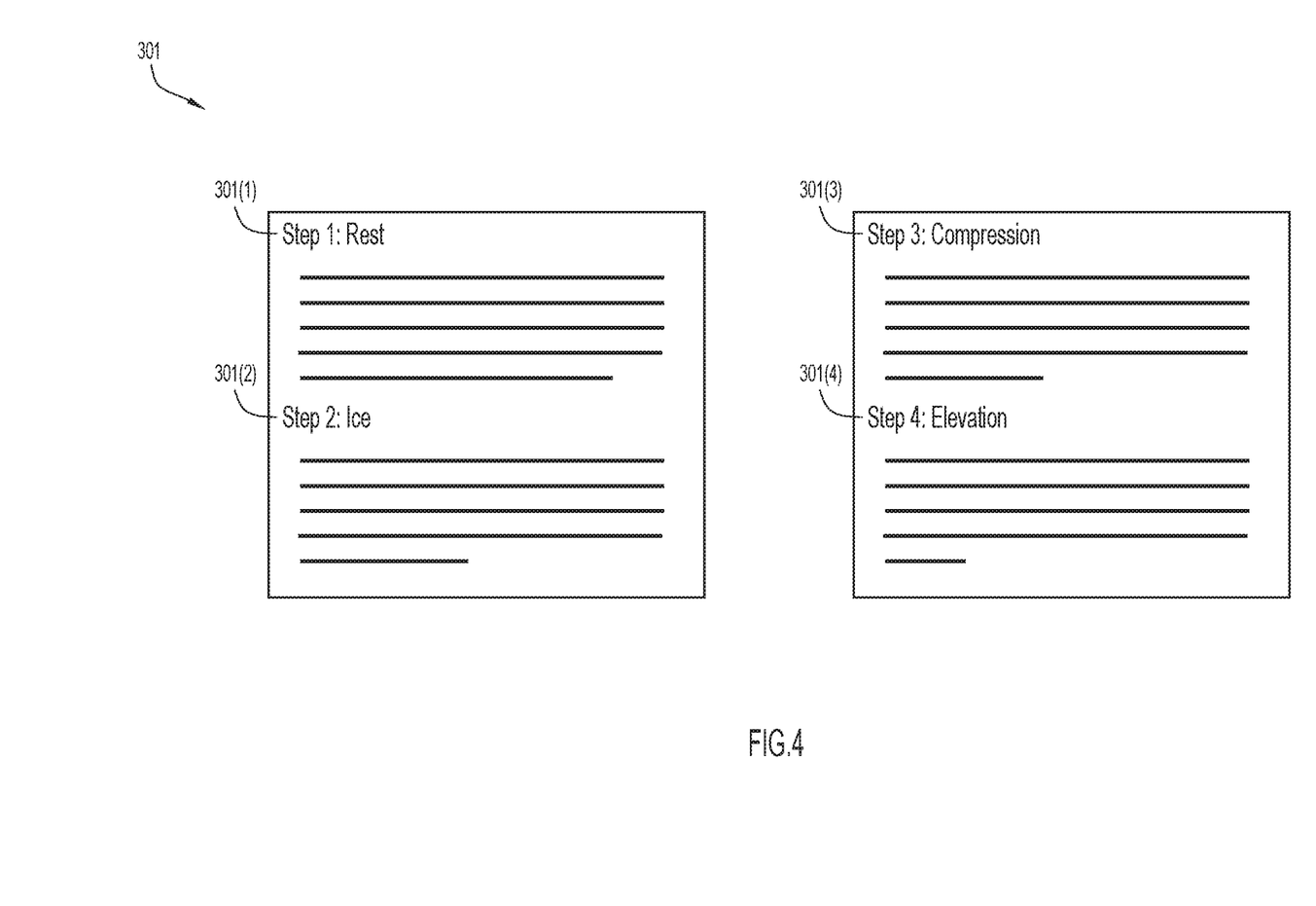
FIG. 4 is an example view of the document of FIG. 3.

FIGS. 3-4 illustrate an example of reformatting presentation of a treatment protocol corresponding to a document according to an example embodiment. FIG. 3 is an example view of the search results 300 including a document 301 that includes a treatment protocol associated with a health-related condition. FIG. 4 is an example view of the document 301. Assume in this example that a user of a client system (e.g., client system 12) has tweaked her knee and that she believes that her knee is sprained. Assume also that the user is in search of information on treatment for knee pain and that she is a user without medical education or training. The user may search for one or more documents of interest by providing a set of one or more search terms to a search engine.

In this example, the user accesses a website or web application that has the ability to search a corpus of one or more documents. For example, the user may access the website and may enter into a search field the search terms "knee pain rest medication." The corpus of one or more documents may be identified based at least on the search terms. For example, the corpus of one or more documents may be identified using any currently known or future developed keyword-based search techniques. In this example, the corpus of one or more documents identified based at least on the search terms includes a document that is available on a webpage identified by a uniform resource locator (URL). The corpus of documents returned from the search for "knee pain rest medication" may be presented to the user. The search results 300 of the search for "knee pain rest medication may include content 302 in the form of a preview, summary, or snippet of information from the document 301. In some scenarios, the content 302 presented to the user may be or include at least a portion of the treatment protocol, and the presentation of such summary content without additional information may pose an unreasonable risk of harm to the user caused from misunderstanding the treatment protocol in the proper context. Content for presentation to the user is determined, the content comprising at least a portion of the treatment protocol associated with the heath-related condition. For example, a snippet or summary 302 of a portion of the document 301 that is relevant to the treatment protocol associated with the health-related condition may be determined for presentation to the user. The snippet or summary may be content that may be part of or include information presented as a search result.

Specifically, in this example, the summary or snippet 302 includes a portion of the treatment protocol corresponding to step 4, elevation. However, presenting step 4 of the protocol to the user may have a risk associated with it that may be unacceptable. For example, step 4 may be dependent on earlier steps of the treatment protocol, and the dependency may lead to an unreasonable risk. As shown in FIG. 4, the document 301 showing all four steps of a treatment protocol. The four steps are: "Step 1: Rest"; "Step 2: Ice"; "Step 3: Compression"; and "Step 4: Elevation". In this example, it is determined that there is a risk above an acceptable threshold of risk in presenting the content 302 without additional information. In response to this determination, the user is presented with a modified or reformatted view that includes information or content 304. In other words, the search result that is to be presented is modified in such a way that reduces the risk associated with the user improperly following the protocol. In this example, the modified view includes a list of the headings of the steps of the protocol 306 and a warning 308. For each step of the protocol, the list 306 may include a link to the relevant portion of the document. For example, the portion 306(1) of the list corresponds to the "Step 1—Rest" and may be a link that is selectable by a user to take the user to the part 301(1) of the document 301 shown in FIG. 4. Likewise, the portions 306(2), 306(3), and 306(4), may each be a link that is selectable by a user to take the user to the part 301(2), 301(3), and 301(4), respectively.

As another example, if the reformatting results in content that cannot be displayed on a single screen or is otherwise determined to be undesirable in its display, the reformatting module 18 may determine not to display the reformatted content together. Instead, the user may be required to open the document to see its content, or do an "accordion style" presentation of the steps, where the user is required to view steps individually and in order. For example, the user would be required to acknowledge a first step has been viewed before being presented with a proceeding step.

Figure 5:
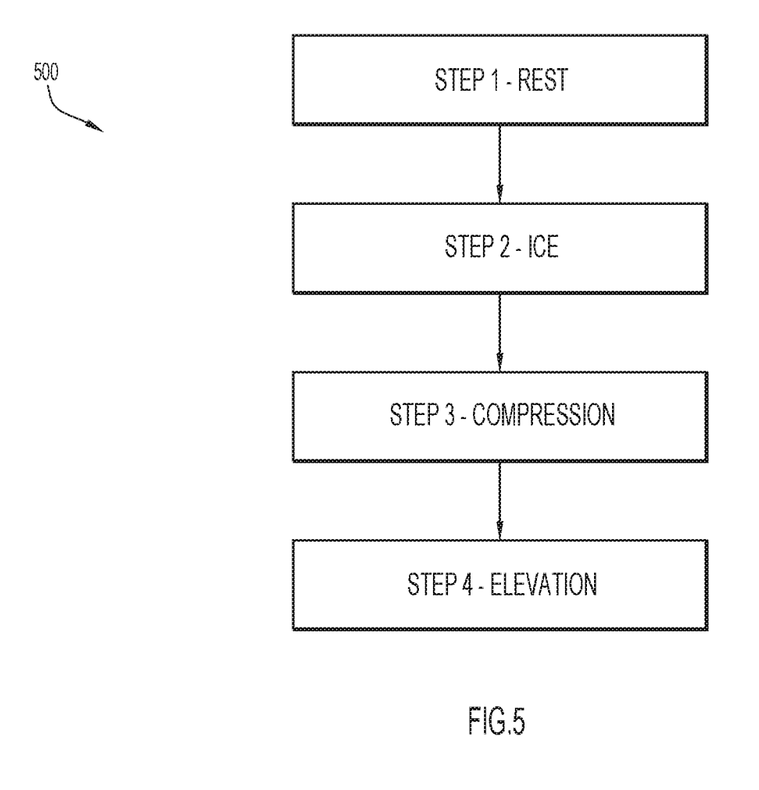
FIG. 5 is an example tree representation of a treatment protocol according to an embodiment of the present invention.

Referring now to FIG. 5, a tree representation 500 of each of the steps or treatments in the treatment protocol extracted from the document 301 is shown. A tree representation may be generated that shows a degree of relationship between steps, including, for example, how entwined the steps are. Prior steps with risk may have a compounding effect on risk of a subsequent step(s). For example, to calculate risk of a to-be presented or viewable step, a step with risk language may be assigned a value of 1, otherwise a step is assigned a value of 0, and prior steps with risk may be assigned a value equal to 2 times the distance from the viewable step. Multiple tree representations can be generated for a single document. For example, a single document may include multiple treatment protocols, and a tree representation can be generated for each treatment protocol present in the document. The tree representation 500 may be generated by the treatment protocol determination module 16 using e.g., natural language processing techniques, to represent relationships between steps of the treatment protocol. For example, the tree representation 500 may indicate the order of the steps, and may be used to determine a dependency of one step to one or more other steps. In this example, the tree representation 500 indicates that the order of the treatment protocol extracted from document 301 is rest, ice, compression, and elevation. In other words, rest is fist, followed by ice, then compression, and last elevation. The tree representation 500 may allow for streamlined risk analysis. For example, after the tree representation 500 is generated, it may be used in risk analysis for subsequent searches that identify the document 301.

The tree representation 500 may be used to determine a number of steps of a protocol from which a step of the protocol depends, which may be used in determining a risk of presenting the step without those steps. For example, risk may be determined for presenting a fourth step of a treatment protocol without any steps from which the fourth step depends, such as the preceding three steps. If the determined risk is unacceptable (e.g., above an acceptable risk threshold), then, for example, risk may be determined for presenting the fourth step with additional information that includes some or all of the preceding three steps as indicated by the tree representation.

Referring now to FIG. 6, a schematic of an example of a computing device 610 of computing environment of FIG. 1 (e.g., implementing server system 10 and/or client system 12) is shown. The computing device is only one example of a suitable computing device for computing environment of FIG. 1 and is not intended to suggest any limitation as to the scope of use or functionality of embodiments of the invention described herein. Regardless, computing device 610 is capable of being implemented and/or performing any of the functionality set forth herein.

In computing device 610, there is a computer system 612 which is operational with numerous other general purpose or special purpose computing system environments or configurations. Examples of well-known computing systems, environments, and/or configurations that may be suitable for use with computer system 612 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 612 may be described in the general context of computer system executable instructions, such as program modules, being executed by a computer system. Generally, program modules may include routines, programs, objects, components, logic, data structures, and so on that perform particular tasks or implement particular abstract data types.

As shown in FIG. 6, computer system 612 is shown in the form of a general-purpose computing device. The components of computer system 612 may include, but are not limited to, one or more processors or processing units 15, a system memory 35, and a bus 618 that couples various system components including system memory 35 to processor 15.

Bus 618 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 612 typically includes a variety of computer system readable media. Such media may be any available media that is accessible by computer system 612, and it includes both volatile and non-volatile media, removable and non-removable media.

System memory 35 can include computer system readable media in the form of volatile memory, such as random access memory (RAM) 630 and/or cache memory 632. Computer system 612 may further include other removable/non-removable, volatile/non-volatile computer system storage media. By way of example only, storage system 634 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 618 by one or more data media interfaces. As will be further depicted and described below, memory 35 may include at least one program product having a set (e.g., at least one) of program modules that are configured to carry out the functions of embodiments of the invention.

Program/utility 640, having a set (at least one) of program modules 642 (e.g., determination module 16, risk analysis module 17, reformatting module 18, user input module 19, presentation module 20, etc.) may be stored in memory 35 by way of example, and not limitation, as well as an operating system, one or more application programs, other program modules, and program data. Each of the operating system, one or more application programs, other program modules, and program data or some combination thereof, may include an implementation of a networking environment. Program modules 642 generally carry out the functions and/or methodologies of embodiments of the invention as described herein.

Computer system 612 may also communicate with one or more external devices 214 such as a keyboard, a pointing device, a display 624, etc.; one or more devices that enable a user to interact with computer system 612; and/or any devices (e.g., network card, modem, etc.) that enable computer system 612 to communicate with one or more other computing devices. Such communication can occur via Input/Output (I/O) interfaces 622. Still yet, computer system 612 can communicate with one or more networks such as a local area network (LAN), a general wide area network (WAN), and/or a public network (e.g., the Internet) via network adapter 25. As depicted, network adapter 25 communicates with the other components of computer system 612 via bus 618. It should be understood that although not shown, other hardware and/or software components could be used in conjunction with computer system 612. Examples, include, but are not limited to: microcode, device drivers, redundant processing units, external disk drive arrays, RAID systems, tape drives, and data archival storage systems, etc.

It will be appreciated that the embodiments described above and illustrated in the drawings represent only a few of the many ways of implementing embodiments for visually displaying healthcare protocols to a user.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, profile generation module, profile comparison module, etc.). These systems may include any types of monitors and input devices (e.g., keyboard, mouse, voice recognition, etc.) to enter and/or view information.

It is to be understood that the software (e.g., modules 16, 17, 18, 19, and 20) of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments (e.g., modules 16, 17, 18, 19, and 20) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, databases or storage structures (e.g., files, databases, data structures, data or other repositories, etc.) to store information (e.g., risk information, documents, reformatted presentations, reformatting information, etc.). The database system may be implemented by any number of any conventional or other databases, databases or storage structures (e.g., files, databases, data structures, data or other repositories, etc.) to store information (e.g., risk information, documents, reformatted presentations, reformatting information). The database system may be included within or coupled to the server and/or client systems. The database systems and/or storage structures may be remote from or local to the computer or other processing systems, and may store any desired data (e.g., risk information, documents, reformatted presentations, reformatting information).

The present invention embodiments may employ any number of any type of user interface (e.g., Graphical User Interface (GUI), command-line, prompt, etc.) for obtaining or providing information (e.g., risk information, documents, reformatted presentations, reformatting information), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The report may include any information arranged in any fashion, and may be configurable based on rules or other criteria to provide desired information to a user (e.g., text analytics, profile scores, demographic information pertaining to the document author, etc.).

The present invention embodiments are not limited to the specific tasks or algorithms described above, but may be utilized for presentation of any type of content. Additionally, while an example embodiment including one or more server systems is shown and described, it will be appreciated that present invention embodiments may be implemented in environments without server systems.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of visually displaying healthcare protocols to a user, the method comprising:
   receiving from the user, via an electronic communications network, one or more search terms associated with a health-related condition;
   identifying, with a computer via a search engine, a corpus of one or more documents stored in an electronic format that satisfies the one or more search terms;
   analyzing, with the computer, at least one document of the corpus for a treatment protocol associated with the health-related condition, wherein the treatment protocol includes a plurality of steps to treat the health-related condition;
   determining, with the computer, first content for presentation to the user from the search engine, the first content comprising at least a portion of the treatment protocol associated with the health-related condition, wherein the first content for presentation corresponds to a subset of the plurality of steps of the treatment protocol;

determining, with the computer, a dependency of a step of the subset to a step of the treatment protocol that is not part of the subset;

determining, with the computer, a number of steps in the treatment protocol between the step of the subset and the step in the treatment protocol that is not part of the subset, wherein determining the number of steps includes:

generating a tree representation of the plurality of steps of the treatment protocol indicating order and dependencies of the plurality of steps; and determining the number of steps based on positions in the tree representation of the step of the subset and the step in the treatment protocol that is not part of the subset;

producing, with the computer, markup language of a preview presentation of the treatment protocol including the first content for presentation;

determining, with the computer, a risk value indicative of one or more risks associated with the first content for presentation, wherein the one or more risks are associated with the user improperly following the treatment protocol and the risk value is based on a combination of risk values assigned to individual terms of the first content for presentation and the determined number of steps in the treatment protocol between the step of the subset and the step of the treatment protocol that is not part of the subset;

determining, with the computer, that the risk value exceeds a risk threshold;

determining, with the computer, second content for presentation by reformatting the first content for presentation from the search engine;

modifying, with the computer, the markup language of the preview presentation of the treatment protocol;

sending, by the computer, a message including the modified markup language to a web browser of a client device of the user to visually display the second content to the user with each step of the second content having a corresponding link;

determining, with the computer, that the second content exceeds a screen area; and in response to the second content exceeding the screen area:

displaying the second content on a plurality of screens on the client device by presenting each step of the second content of the modified markup language individually on a different one of the plurality of screens with the corresponding link, wherein each successive step of the second content is displayed in response to user acknowledgment of a corresponding prior step; and when the corresponding link of a corresponding step is actuated, directing the user to a location in a corresponding document containing the corresponding step.

2. The method of claim 1, wherein the second content includes the first content.

3. The method of claim 1, wherein the second content is different than the first content.

4. The method of claim 1, wherein determining the second content for presentation by reformatting the first content for presentation comprises including at least one of a risk warning or a waiver.

5. The method of claim 1, wherein determining the second content for presentation comprises including at least one of the plurality of steps of the treatment protocol that is not part of the subset.

6. The method of claim 1, wherein analyzing at least one document of the corpus for a treatment protocol associated with a health-related condition comprises extracting the treatment protocol from a document based on at least one of a document heading, a numbered formatting, a numbered hierarchy, a bulleted list, an action element, or a declarative statement.

7. The method of claim 1, wherein analyzing at least one document of the corpus for a treatment protocol associated with a health-related condition comprises segmenting the treatment protocol into a plurality of segments, and wherein determining second content for presentation by reformatting the first content for presentation comprises augmenting the segments with visual elements to visually indicate one or more risks associated with the segments.

8. The method of claim 1, wherein determining a risk value indicative of one or more risks associated with the first content for presentation comprises:

identifying in a document a set of one or more terms for risk analysis; and comparing the set of one or more terms for risk analysis with a plurality of terms of a risk database.

9. The method of claim 1, wherein determining second content for presentation by reformatting the first content for presentation comprises determining to present one or more steps of the treatment protocol prior to the subset of steps.

10. The method of claim 1, wherein modifying the markup language of the preview presentation of the treatment protocol comprises modifying the markup language of the preview presentation of the treatment protocol to disallow presentation of the first content in the preview presentation.

11. The method of claim 1, further comprising:

storing the reformatted first content;

receiving one or more second search terms;

determining that a search based on the one or more second search terms had been previously performed based on a comparison of the one or more second search terms to the one or more search terms; and providing the stored reformatted first content as a result for the one or more second search terms without determination and evaluation of the risk value.

12. A system for visually displaying healthcare protocols to a user, the system comprising at least one processor configured to:

receive from the user, via an electronic communications network, one or more search terms associated with a health-related condition;

identify, via a search engine, a corpus of one or more documents that satisfies the one or more search terms;

analyze at least one document of the corpus for a treatment protocol associated with the health-related condition, wherein the treatment protocol includes a plurality of steps to treat the health-related condition;

determine first content for presentation to the user from the search engine, the first content comprising at least a portion of the treatment protocol associated with the health-related condition, wherein the first content for presentation corresponds to a subset of the plurality of steps of the treatment protocol;

determine a dependency of a step of the subset to a step of the treatment protocol that is not part of the subset;

determine a number of steps in the treatment protocol between the step of the subset and the step in the treatment protocol that is not part of the subset, wherein determining the number of steps includes:

generating a tree representation of the plurality of steps of the treatment protocol indicating order and dependencies of the plurality of steps; and determining the number of steps based on positions in the tree representation of the step of the subset and the step in the treatment protocol that is not part of the subset;

produce markup language of a preview presentation of the treatment protocol including the first content for presentation;

determine a risk value indicative of one or more risks associated with the first content for presentation, wherein the one or more risks are associated with the user improperly following the treatment protocol and the risk value is based on a combination of risk values assigned to individual terms of the first content for presentation and the determined number of steps in the treatment protocol between the step of the subset and the step of the treatment protocol that is not part of the subset;

determine that the risk value exceeds a risk threshold;

determine second content for presentation by reformatting the first content for presentation from the search engine;

modify the markup language of the preview presentation of the treatment protocol;

send a message including the modified markup language to a web browser of a client device of the user to visually display the second content to the user with each step of the second content having a corresponding link;

determine that the second content exceeds a screen area; and in response to the second content exceeding the screen area:

display the second content on a plurality of screens on the client device by presenting each step of the second content of the modified markup language individually on a different one of the plurality of screens with the corresponding link, wherein each successive step of the second content is displayed in response to user acknowledgment of a corresponding prior step; and when the corresponding link of a corresponding step is actuated, direct the user to a location in a corresponding document containing the corresponding step.

13. The system of claim 12, wherein the at least one processor is configured to determine second content for presentation by reformatting the first content for presentation to include at least one of a risk warning or a waiver.

14. The system of claim 12, wherein the at least one processor is configured to determine the second content for presentation by reformatting the first content to include at least one of the plurality of steps of the treatment protocol that is not part of the subset.

15. The system of claim 12, wherein the at least one processor is configured to determine second content for presentation by reformatting the first content for presentation by determining to present one or more steps of the treatment protocol prior to the subset of steps.

16. A computer program product for visually displaying healthcare protocols to a user, the computer program product comprising one or more computer readable storage media having program instructions collectively stored on the one or more computer readable storage media, the program instructions executable by a processor to cause the processor to:

receive from the user, via an electronic communications network, one or more search terms associated with a health-related condition;

identify, via a search engine, a corpus of one or more documents that satisfies the one or more search terms;

analyze at least one document of the corpus for a treatment protocol associated with the health-related condition, wherein the treatment protocol includes a plurality of steps to treat the health-related condition;

determine first content for presentation to the user from the search engine, the first content comprising at least a portion of the treatment protocol associated with the health-related condition, wherein the first content for presentation corresponds to a subset of the plurality of steps of the treatment protocol;

determine a dependency of a step of the subset to a step of the treatment protocol that is not part of the subset;

determine a number of steps in the treatment protocol between the step of the subset and the step in the treatment protocol that is not part of the subset, wherein determining the number of steps includes:

generating a tree representation of the plurality of steps of the treatment protocol indicating order and dependencies of the plurality of steps; and determining the number of steps based on positions in the tree representation of the step of the subset and the step in the treatment protocol that is not part of the subset;

produce markup language of a preview presentation of the treatment protocol including the first content for presentation;

determine a risk value indicative of one or more risks associated with the first content for presentation, wherein the one or more risks are associated with the user improperly following the treatment protocol and the risk value is based on a combination of risk values assigned to individual terms of the first content for presentation and the determined number of steps in the treatment protocol between the step of the subset and the step of the treatment protocol that is not part of the subset;

determine that the risk value exceeds a risk threshold;

determine second content for presentation by reformatting the first content for presentation from the search engine;

modify the markup language of the preview presentation of the treatment protocol;

send a message including the modified markup language to a web browser of a client device of the user to visually display the second content to the user with each step of the second content having a corresponding link;

determine that the second content exceeds a screen area; and in response to the second content exceeding the screen area:

display the second content on a plurality of screens on the client device by presenting each step of the second content of the modified markup language individually on a different one of the plurality of screens with the corresponding link, wherein each successive step of the second content is displayed in response to user acknowledgment of a corresponding prior step; and when the corresponding link of a corresponding step is actuated, direct the user to a location in a corresponding document containing the corresponding step.

17. The computer program product of claim 16, wherein the program instructions are executable by a processor to cause the processor to determine second content for presentation by reformatting the first content for presentation to include at least one of a risk warning or a waiver.

18. The computer program product of claim 16, wherein the program instructions are executable by a processor to cause the processor to determine the second content for presentation by reformatting the first content to include at least one of the plurality of steps of the treatment protocol that is not part of the subset.

* * * * *